United States Patent
Van Der Hauw et al.

(10) Patent No.: US 10,722,873 B2
(45) Date of Patent: Jul. 28, 2020

(54) CATALYST COMPOSITION AND ISOMERISATION PROCESS

(71) Applicant: SHELL OIL COMPANY, Houston, TX (US)

(72) Inventors: Menno Feico Van Der Hauw, Amsterdam (NL); Richard Berend Mauer, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/060,088

(22) PCT Filed: Dec. 8, 2016

(86) PCT No.: PCT/EP2016/080197
§ 371 (c)(1),
(2) Date: Jun. 7, 2018

(87) PCT Pub. No.: WO2017/097880
PCT Pub. Date: Jun. 15, 2017

(65) Prior Publication Data
US 2018/0369797 A1 Dec. 27, 2018

(30) Foreign Application Priority Data

Dec. 11, 2015 (EP) .................................... 15199643

(51) Int. Cl.

| | | |
|---|---|---|
| *B01J 29/06* | (2006.01) | |
| *B01J 29/80* | (2006.01) | |
| *C07C 5/27* | (2006.01) | |
| *B01J 29/74* | (2006.01) | |
| *B01J 35/00* | (2006.01) | |
| *B01J 37/00* | (2006.01) | |
| *C07C 15/08* | (2006.01) | |
| *B01J 37/02* | (2006.01) | |

(52) U.S. Cl.
CPC .......... *B01J 29/80* (2013.01); *B01J 29/7446* (2013.01); *B01J 29/7469* (2013.01); *B01J 35/0006* (2013.01); *B01J 37/0009* (2013.01); *B01J 37/02* (2013.01); *C07C 5/2708* (2013.01); *C07C 15/08* (2013.01); *B01J 2229/20* (2013.01); *B01J 2229/42* (2013.01); *C07C 2529/74* (2013.01); *C07C 2529/80* (2013.01); *Y02P 20/52* (2015.11)

(58) Field of Classification Search
CPC .... B01J 29/80; B01J 29/7446; B01J 29/7469; B01J 2229/20; B01J 2229/42; B01J 35/0006; B01J 37/0009; B01J 37/02; C07C 5/2708; C07C 15/08; C07C 2529/74; C07C 2529/80; Y02P 20/52
USPC ............... 502/60, 63, 64, 66, 69, 71, 74, 67; 585/477, 480, 481, 482
See application file for complete search history.

(56) References Cited

U.S. PATENT DOCUMENTS

| | | | | |
|---|---|---|---|---|
| 7,982,083 B2 * | 7/2011 | Guillon | ..................... | B01J 29/80 502/60 |
| 2009/0093661 A1 * | 4/2009 | Guillon | ..................... | B01J 29/80 585/477 |
| 2009/0299115 A1 * | 12/2009 | Guillon | ..................... | B01J 29/80 585/481 |
| 2012/0283498 A1 * | 11/2012 | Guillon | .................. | B01J 27/224 585/481 |
| 2013/0041194 A1 * | 2/2013 | Ballegoy | .............. | B01J 29/7469 585/477 |
| 2013/0261364 A1 * | 10/2013 | Ercan | ....................... | B01J 37/04 585/475 |
| 2016/0272558 A1 * | 9/2016 | Bender | ................ | B01J 19/2445 |

* cited by examiner

*Primary Examiner* — Elizabeth D Wood
(74) *Attorney, Agent, or Firm* — Charles W. Stewart

(57) ABSTRACT

The invention relates to a catalyst composition which comprises a carrier material component and at least one metal component that is supported on the carrier material component. The carrier material component comprises a ZSM-12 type zeolite, a EU-1 type zeolite, and an inorganic binder. The metal component may include a Group VIII metal. The invention further relates to a process for preparing the catalyst and using it in a process for the isomerisation of alkylaromatics.

19 Claims, 2 Drawing Sheets

CATALYST COMPOSITION AND ISOMERISATION PROCESS

PRIORITY CLAIM

Figure 1:
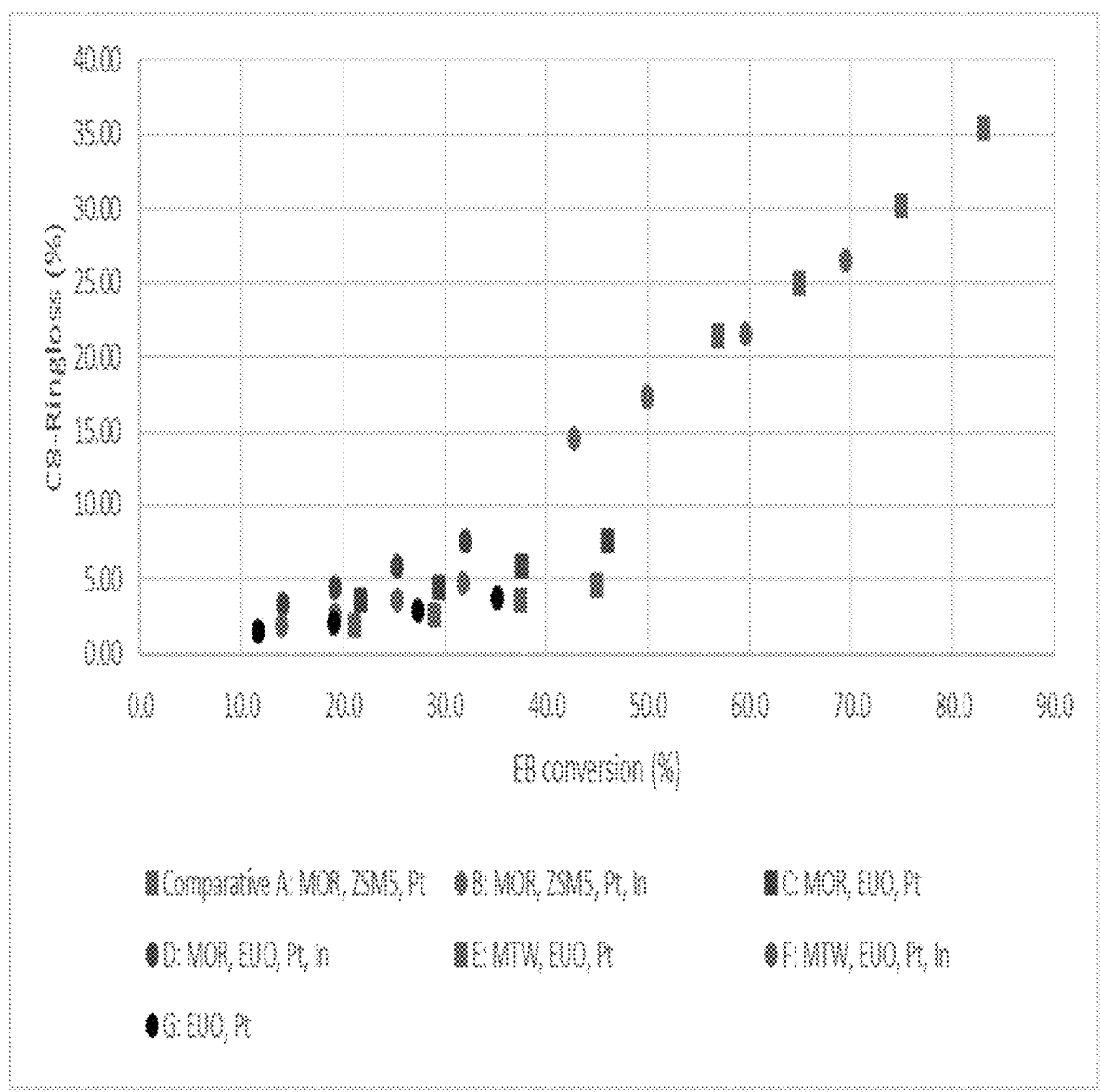
Figure 2:
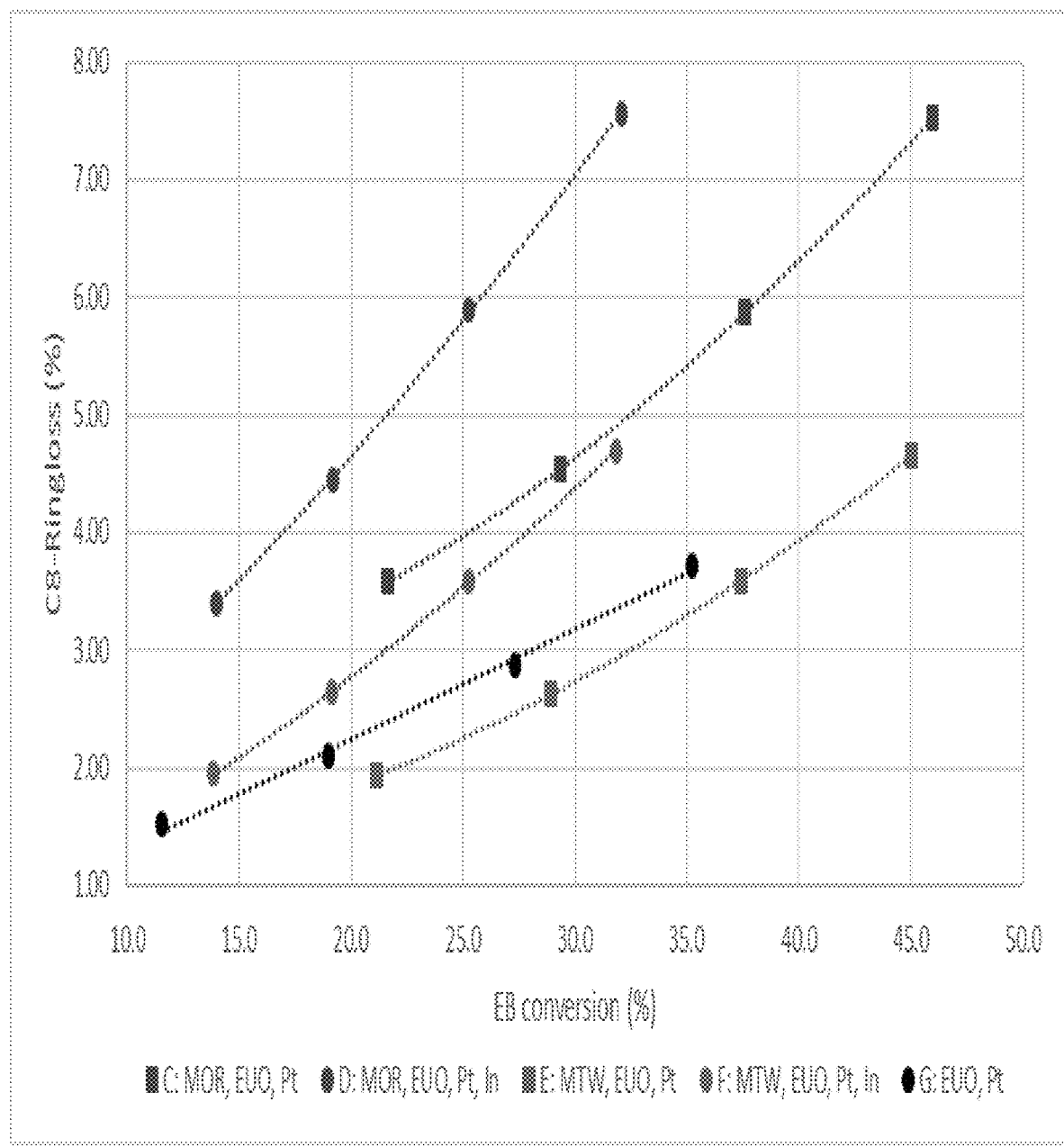

The present application is the National Stage (§ 371) of International Application No. PCT/EP2016/080197, filed Dec. 8, 2016, which claims priority from European Patent Application No. 15199643.6, filed Dec. 11, 2015, incorporated herein by reference.

FIELD OF THE INVENTION

The present invention relates to a catalyst composition; a process for preparing the catalyst; and a process for isomerising xylenes and alkyl aromatics using the catalyst.

BACKGROUND OF THE INVENTION

Following fractionation or distillation of crude petroleum oil, a straight-run naphtha fraction, boiling in the 70° C. to 190° C. range, is obtained. This fraction may be catalytically converted to an aromatic reformate.

On conversion to reformate, the aromatics content is considerably increased and the resulting hydrocarbon mixture becomes highly desirable as a source of valuable chemical intermediates and as a component for gasoline.

Heart-cut reformate generally contains aromatic hydrocarbons having 8 carbon atoms such as ethylbenzene and xylenes. Other components may be present such as their hydrogenated homologues such as naphthenes.

Within the xylenes, para-xylene is the most useful commodity and isomerisation or transalkylation processes have been developed to increase the proportion of para-xylene. However, isomerisation or transalkylation processes can also produce undesired side-products such as compounds having of from 1 to 5 carbon atoms, toluene, compounds having 9 or more carbon atoms and benzene.

Many catalysts have been made and proposed for various reactions involving aromatics, but for some reactions, such as ethylbenzene isomerisation or transalkylation processes, there is commonly a trade-off between providing the desired products and known side reactions. One common side reaction of ethylbenzene hydroisomerisation is the formation of compounds having of from 1 to 5 carbon atoms, which is disadvantageous from an environmental and economic point of view.

U.S. Pat. No. 4,939,110 discloses a catalyst comprising an inorganic oxide binder, a pentasil zeolite, a Group VIII metal and lead for use in the conversion of aromatic hydrocarbons.

U.S. Pat. No. 4,762,957 discloses a process for the isomerisation of alkylaromatics using a catalyst with an alumina matrix, a magnesium-containing zeolite, and a Group VIII metal component.

Whilst reasonable results are presented in these documents, the inclusion of magnesium or iron adds complexity and expense to the catalyst preparation.

WO9745198 discloses a zeolite bound zeolite catalyst for use in hydrocarbon conversion comprising first crystals of a first zeolite, and a binder comprising second crystals of a second zeolite which has a structure type that is different from the structure type of the first zeolite. The first and second zeolites provide a bifunctional catalyst having the capability of performing two or more functions. However, the production of such a zeolite bound zeolite catalyst requires additional complexity and manufacturing steps, so that zeolite bound zeolite catalysts have not apparently been scaled up commercially.

U.S. Pat. No. 3,856,872 describes a xylene isomerization process in which the conventional platinum on silica-alumina is replaced by a zeolite catalyst of the ZSM-5 type or a zeolite ZSM-12 catalyst or zeolite ZSM-21 catalyst. The zeolite can be incorporated in an inert, and therefore non-acidic, alumina matrix. U.S. Pat. No. 3,856,872 contains no teaching on kind or amount of zeolite ZSM-21.

The article "Dealuminated zeolite-based composite catalysts for reforming of an industrial naphthene-rich feedstock" deals with reforming catalysts for naphthenic feedstocks. The preferred ZSM-12 zeolite has a Si/Al ratio of 54. It is taught that ZSM-12 having higher silica to alumina ratios should not be used for such catalysts as this produces large amounts of $CH_4$ and less aromatics.

SUMMARY OF THE INVENTION

An object of the present invention is to provide an improved catalyst for the isomerisation of alkylaromatics such as ethylbenzene and meta-xylene which can provide xylenes especially para-xylene.

It has now been found that this object can be realized by a catalyst comprising different types of zeolite.

Accordingly, the present invention provides a catalyst composition which comprises a carrier material component and a metal(s) component that is supported on the carrier material component, wherein the carrier material component comprises (i) a ZSM-12 type zeolite in an amount of from 2 to 20% by weight (% wt), based on total weight of carrier material component, the ZSM-12 type zeolite having a silica to alumina molar ratio in the range of from 60 to 200; (ii) a EU-1 type zeolite in an amount of from 2 to 30% wt, based on total weight of carrier material component, the EU-1 type zeolite having a silica to alumina molar ratio in the range of from 20 to 200; and (iii) an inorganic binder in an amount in the range of from 55 to 96% wt, based on total weight of carrier material component; and wherein the metal(s) component comprises a Group VIII metal in an amount of at least 0.01% wt, based on total weight of catalyst composition.

DETAILED DESCRIPTION OF THE INVENTION

The particular combination of zeolites has been found to be beneficial in providing a catalyst for the isomerisation of alkylaromatics at relatively high weight hourly space velocity feed throughputs, especially in relation to alkylaromatics containing 8 carbon atoms. This particular combination of zeolites has been found to provide a catalyst for the isomerisation of alkylaromatics containing 8 carbon atoms which catalyst may increase the conversion of ethylbenzene. It was also observed that the particular combination of zeolites increased the production of desired products such as para-xylene. Furthermore, the catalyst may reduce side reactions such as the formation of compounds containing of from 1 to 5 carbon atoms, and thus any unwanted creation of carbon dioxide, and/or reduce the formation of benzene, and/or increase and/or improve the separation of desired product from the reaction mixture such as para-xylene.

One or more of the above can lead to an increase in the final product of the yield of desired compound such as para-xylene.

An increase in ethylbenzene conversion is not only a desired advantage in its own right, but also reduces the amount of a major competitive absorbent in the reaction mixture for the subsequent separation. Separating para-xylene, in particular from a reaction mixture predominantly consisting of compounds containing 8 carbon atoms, by using molecular sieves is known to be difficult because of the presence of competitive absorbents, such as remaining ethylbenzene, which reduces the efficiency of the separation process. Thus, creating less competitive absorbents in the reaction mixture makes it significantly easier to separate the desired products such as para-xylene.

Some side products, such as toluene, benzene and aromatic compounds containing 9 or more carbon atoms, can also be useful commercial products, such that their formation in isomerisation of compounds containing 8 carbon atoms is still useful.

The present invention is not limited to alkylaromatics containing 8 carbon atoms but may include the isomerisation of other alkylaromatics such as alkylaromatics containing 9 carbon atoms or more, including alkylaromatics containing 9 or 10 carbon atoms, which are known to follow similar reaction paths, and to use the same or similar catalyst formulations. Therefore, the present invention relates to isomerisation of alkylaromatics in general, more specifically alkylaromatics comprising of from 8 to 10 carbons, more specifically alkylaromatics comprising 8 or 9 carbon atoms.

The inorganic binder may be selected from any of the suitable metal oxides known in the art. Examples of preferred inorganic binders are alumina silica, alumina, titania, zirconia, ceria, gallia and any mixture thereof.

Preferably, the binder consists of alumina with up to 50% wt of other compounds, more specifically up to 20% wt, more specifically up to 10% wt, most specifically up to 5% wt. Preferably, the binder consists of alumina.

Alumina can be prepared in a number of forms. The alumina grades available differ in parameters such as pore volume, average pore diameter, bulk density, and surface area. Although different alumina manufacturers can provide the same or similar alumina products under different nomenclature, different products classifications can have the same or similar or overlapping criteria and/or properties. For example, "high pore" and "wide pore" aluminas tend to have the same or similar properties.

The present invention extends to the use of alumina as the inorganic binder from any source, and examples of suitable alumina binders include grades of the Pural range from Sasol, such as the KR and SB grades, and other wide pore aluminas such as WPA from Criterion.

In a preferred embodiment of the present invention, the pore volume of the inorganic binder as measured with the help of nitrogen is at least 0.6 cc/g, preferably at least 1.2 cc/g. The pore volume of the inorganic binder preferably is up to 2 cc/g, preferably up to 1.6 cc/g. These ranges of pore volume of the inorganic binder include "wide pore" alumina, which has a more open structure thereby allowing greater interaction with the alkylaromatics.

In another embodiment of the present invention, the average pore diameter of the inorganic binder is greater than 80 Å, preferably greater than 90 Å.

In a further embodiment of the present invention, the bulk density of the inorganic binder is less than 0.3 g/cc, preferably less than 0.25 g/cc. The catalyst composition according to the present invention contains an inorganic binder in an amount in the range of from 55 to 96% wt, based on total weight of carrier material component. Preferably, the inorganic binder is present in an amount in the range of from 65 to 96% wt, more preferably in the range of from 80 to 91% wt, based on total carrier material component. In a yet further embodiment of the present invention, the inorganic binder is present in the amount of more than 80% wt, preferably more than 85% wt, especially at least 90% wt, based on total amount of catalyst.

The present catalyst composition includes at least 0.01% wt of a Group VIII metal of the Periodic Table of the Elements. Preferably, the amount of Group VIII metal is at most 10% wt. The amount is the amount of metal on total weight of catalyst. Reference to "Group VIII" as used herein relates to the current IUPAC version of the Periodic Table. Preferred catalytically active metals are nickel, palladium and/or platinum. The most preferred metal is platinum. Combinations of two or more catalytically active metals are also possible, preferably being platinum metal combinations. The catalytically active metal may also be provided in the form of a compound, optionally requiring activation prior to use.

In one embodiment to the present invention, the Group VIII metal is present in the catalyst in an amount in the range of from 0.1 to 0.6% wt based on total weight of catalyst composition.

The ZSM-12 type zeolite is a well-known zeolite, generally having an aluminosilicate basis, optionally including one or more other elements. Many methods of making various forms of ZSM-12 are known in the art. By way of example only, WO2004046034 provides a discussion of the formation of certain forms of ZSM-12, and is included herein by way of reference.

The EU-1 type zeolite is also a well-known zeolite, generally having an aluminosilicate basis. Methods of preparing EU-1 type zeolite are known in the art. By way of example only, EP0042226 provides a discussion of the formation of various types of EU-1, and is included herein by way of reference.

Each ZSM-12 and EU-1 are as defined in the Atlas of Zeolite Framework Types, sixth revised edition 2007.

The catalyst could be provided by admixture of the inorganic binder and zeolite components, following by shaping, and then typically drying and calcining the pre-formed product. Optionally, the addition of the Group VIII metal is carried out after drying and/or calcining of the catalyst pre-formed, and optionally there is a further calcination thereafter. Preferably, the Group VIII metal is incorporated by pore volume impregnation.

Preferably, the present catalyst carrier is prepared by extrusion. Therefore, the catalyst carrier preferably is an extrudate.

It is known that the crystal morphology of a zeolite influences its activity and stability. In the present invention, it is particularly preferred that the ZSM-12 type zeolite has an average particle size in the range of from 5 to 50 nm, more preferably in the range of from 10 to 45 nm, and most preferably in the range of from 20 to 40 nm. The ZSM-12 preferably has a surface area as measured with the help of nitrogen adsorption (ASTM D3663-03(2015)) of more than 250 $m^2/g$, preferably more than 280 $m^2/g$. The crystallinity preferably is greater than 94%, more preferably greater than 97%.

In the present invention, it is particularly preferred that the EU-1 type zeolite has a number average particle size in the range of from 5 to 120 nm, more preferably in the range of from 10 to 90 nm, and most preferably in the range of from 20 to 70 nm. Preferably, the surface area as measured with the help of nitrogen adsorption (ASTM D3663-03(2015)) is more than 350 $m^2/g$, preferably more than 380 $m^2/g$. The crystallinity preferably is greater than 94%, preferably greater than 97%.

The average particle size is determined by calculating the number average crystal size of a sample which has been measured by Transmission Electron Microscopy (TEM).

The provision of zeolites having defined parameters such as those described above in relation to zeolite crystal morphology is known to those skilled in the art and is not further described herein.

The amount of the ZSM-12 type zeolite is preferably in the range of from 2 to 20% wt, preferably of from 2 to 15% wt, more preferably of from 4 to 11% wt, based on total carrier material component.

The amount of the EU-1 type zeolite is preferably in the range of from 2 to 24% wt, preferably of from 2 to 20% wt, more preferably of from 4 to 15% wt, based on total carrier material component.

Preferably, the sum of the amounts of the ZSM-12 type zeolite and EU-1 type zeolite is less than 45% wt, more preferably in the range of from 4 to 30% wt, more preferably of from 10 to 25% wt. The total amount of binder preferably is of from 70 to 95% wt, more preferably of from 75 to 90% wt.

Whilst the catalyst of the present invention may include a minor or very small amount zeolites other than ZSM-12 and EU-1, the catalyst preferably comprises only ZSM-12 and EU-1 as the zeolites.

Another parameter of the zeolites are their silica to alumina molar ratio (SAR). The bulk or overall SAR can be determined by any one of a number of chemical analysis techniques. Such techniques include X-ray fluorescence, atomic adsorption, and inductive coupled plasma-atomic emission spectroscopy (ICP-AES). All will provide substantially the same bulk ratio value. The silica to alumina molar ratio for use in the present invention is determined by X-ray fluorescence.

It is a particular feature of the present invention that the SAR of the ZSM-12 type zeolite is in the range of from 60 to 200, preferably in the range of from 70 to 150. The SAR of the EU-1 type zeolite is in the range of from 20 to 200, preferably in the range of from 20 to 150. It can be advantageous that the EU-1 type zeolite has a SAR in the range of from 20 to 95, more specifically of from 25 to 50.

Inorganic binders such as those based on alumina are also acidic, and so will contribute to the reaction as well. Similarly, it is generally expected that a higher loading of zeolites in the catalyst will increase the catalyst activity and/or yield, so that the skilled person is directed in the art to considering having a significant proportion of the catalyst being the zeolite components.

The catalyst of the present invention is particularly suitable for the isomerisation of ethylbenzene to xylenes, and for the isomerisation of xylenes to equilibrium. Further particularly, the catalyst of the present invention is suitable for use to provide para-xylene from ethylbenzene and other isomers of xylene commonly provided in mixed-component streams.

According to a second aspect of the present invention, there is provided a process for the isomerisation of alkylaromatics to provide a reaction mixture, which process comprises contacting a hydrocarbon stream comprising alkylaromatics with a catalyst composition according to the present invention.

The hydrocarbon stream may comprise any amount of ethylbenzene, such as more than 60% wt based on total amount of feedstock. The hydrocarbon stream specifically contains at most 60% wt of ethylbenzene, more specifically at most 50% wt. Preferably, the hydrocarbon stream comprises at least 1% wt of ethylbenzene, more preferably at least 2% wt, more preferably at least 3% wt, more specifically at least 5% wt, more specifically at least 8% wt, preferably at least 10% wt, most preferably at least 15% wt.

In one embodiment of the process of the present invention, the hydrocarbon stream is contacted with the catalyst at a temperature in the range of from 300 to 450° C., preferably in the range of from 350 to 400° C.

In another embodiment, preferably at least 20% of the ethylbenzene in the feed is converted into xylenes, more specifically at least 25%, more specifically at least 30%, more specifically at least 35% and most specifically at least 40%.

In a further embodiment, the ratio of para-xylene to ethylbenzene in the reaction mixture obtained is more than 1.3, preferably more than 1.5 and most preferably more than 2.

The present catalyst composition may be shaped in any particular form. Suitable shapes include trilobes and cylinders, Preferably, the present catalyst composition is in the shape of trilobes.

It has been found that the combined use of a ZSM-12 type zeolite and a EU-1 type zeolite as carrier material components surprisingly can result in a higher benzene conversion and selectivity towards para-xylene than might be expected from each these carrier material components separately.

The catalyst composition according to the invention can suitably have such shape that a reactor filled with the catalyst particles has an average void fraction of at least 10% by volume, preferably in the range of from 20 to 70%, more preferably in the range of from 35 to 55% by volume.

The catalyst composition of the present invention may be prepared using standard techniques for combining the carrier material components and include shaping; compositing with the metals components; and any subsequent useful process steps such as drying, calcining, and reducing.

The present invention also relates to a process for preparing the catalyst according to the present invention, comprising the steps of:
(a) mixing the ZSM-12 type zeolite, EU-1 type zeolite, inorganic binder, and Group VIII, preferably platinum, in any possible sequence; and
(b) calcining the mixture as obtained in step (a).

In step (b), the calcining can suitably carried out at a temperature of from 450 to 1100° C., preferably above 500° C.

The Group VIII metal is suitably present in step (a) in the form of a Group VIII metal salt solution.

In a particular embodiment, after shaping the carrier material component, the carrier material component is subjected to a calcination step, and subsequently the calcined carrier material then is subjected to metal impregnation. After the metal impregnation the catalyst composition so obtained can then first be dried, followed by calcinations. Drying temperatures can suitably be in the range of from 50 to 200° C. Drying times can suitably be in the range of from 0.5 to 5 hours. Calcination temperatures can suitably be in the range of from 200 to 800° C., preferably in the range of from 300 to 600° C. For the first calcination of the carrier material, a relatively short time can suitably be applied in the range of from 0.5 to 3 hours. For second calcination of the catalyst composition as such a longer time can suitably applied for instance in the range of from 5 to 20 hours 0.5 to 3 hours. The first and second calcinations can suitably be carried out at a temperature in the range of from 400 to 700° C., preferably in the range of from 450 to 650° C.

Before use of the catalyst composition, it will be advantageous to ensure that the metals on the catalyst composition are in metallic (and not oxidic) form. Accordingly, the catalyst composition will be subjected to reducing conditions, which are, for example, heating in a reducing atmosphere, such as in hydrogen optionally diluted by an inert gas, such as nitrogen or carbon dioxide, at temperature in the range of from 150 to 600° C. for a period of time in the range from 0.5 to 5 hours.

A major advantage of the present catalyst composition to be used in the present isomerisation process is the fact that a high weight hourly space velocity can be applied in the process, resulting in a much higher throughput in the reactor and thus a higher production rates. The weight hourly space velocity applied in the process is suitably in the range of from 3 to 12 $hr^{-1}$, more specifically of from 4 to 12 $hr^{-1}$, more specifically of from 5 to 12 $hr^{-1}$.

The present invention will now be illustrated by the following Examples.

EXAMPLES

Example 1

A carrier was prepared by mixing a combination of 5% wt of ZSM-12 having a SAR of 95 and and 95% wt of Criterion WPA alumina, kneading and then shaping the kneaded mixture by extrusion into 1.6 mm cylinders. The extrudates were dried at 120° C. and subsequently calcined at 600° C.

An impregnation solution was prepared comprising hexachloroplatinic acid (H2PtCl6) as the metal source with nitric acid added to obtain pH of 1.6.

The extrudates were pore volume impregnated with this impregnation solution, dried at 120° C. and subsequently calcined at 450° C. for 1 hour.

The final catalyst contained 0.3% wt of platinum based on total weight of catalyst.

Example 2

A carrier was prepared by mixing a combination of 10% wt of ZSM-12 having a SAR of 95, 5% wt of ZSM-5 with SAR of 400 and 85% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 3

A carrier was prepared by mixing a combination of 5% wt of ZSM-12 having a SAR of 95, 5% wt EU-1 with SAR of 33 and 90% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 4

A carrier was prepared by mixing a combination of 5% wt of ZSM-12 having a SAR of 95, 5% wt EU-1 nano crystals having a SAR of 33 and 90% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 5

A carrier was prepared by mixing a combination of 10% wt of ZSM-12 having a SAR of 95, 5% wt EU-1 having a SAR of 33 and 85% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 6

A carrier was prepared by mixing a combination of 5% wt of ZSM-12 having a SAR of 95, 13% wt EU-1 having a SAR of 33 and 82% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 7

A carrier was prepared by mixing a combination of 5% wt of ZSM-12 having a SAR of 95, 13% wt EU-1 having a SAR of 100 and 82% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 8

A carrier was prepared by mixing a combination of 5% wt of ZSM-12 having a SAR of 95, 13% wt ZSM-50 having a SAR of 100 and 82% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 9

A carrier was prepared by mixing a combination of 5% wt of ZSM-12 having a SAR of 95, 13% wt TNU-10 having a SAR of 30 and 82% wt of Criterion WPA alumina, kneading and then shaping the kneaded mixture by extrusion into 1.6 mm cylinders. The extrudates were dried at 120° C. and subsequently calcined at 600° C.

The impregnation was done according to procedure described in Example 1.

Example 10

The catalysts prepared in the Examples above were tested in the isomerisation of an ethylbenzene and mixed xylene feed. The feed comprised 19% wt ethylbenzene (EB), 15.5% wt ortho-xylene (oX), 59% wt meta-xylene (mX) and 6.5% wt ethyl cyclohexane.

The catalytic test was performed in a micro-flow reactor unit encompassing a reactor tube with an internal diameter of 15 mm, into which the catalyst was loaded together with SiC as packing material.

After loading the catalyst was dried at 400° C. for 1.5 hours and then reduced with $H_2$ at 400° C. for 1 hour at a pressure of 8 bar. The reactor was then heated to 425° C. and treated with a mixture of 20% wt EB and 80% wt oX for a period of 24 hours at a weight hourly space velocity (WHSV) of 5 g feed/g catalyst/h and a $H_2$:hydrocarbon ratio of 4 mol/mol to reach a stable operation regime.

Following this, the catalyst was subjected to a temperature of 387° C. and treated with the same EB and mixed xylene mixture described above (19% wt EB, 15.5% wt oX, 59% wt mX and 6.5% wt ethyl cyclohexane) at a WHSV of 8.0 g feed/g catalyst/h at a $H_2$/hydrocarbon ratio of 4 mol/mol.

The catalysts prepared in Examples 1 to 9 were compared for their performance in isomerization at relatively high weight hourly space velocity. Table 1 shows the perfomance of the catalysts of Examples 1 to 9 in ethylbenzene conversion and the degree to which the xylene reaction mixture has reached equilibrium for para-xylene.

Ethylbenzene conversion (EB conversion) is the weight percent of ethylbenzene converted by the catalyst into a xylene i.e. either oX, mX or pX.

pXate is a measure for the degree to which the xylene reaction mixture has reached equilibrium for para-xylene. It is defined as follows:

$$pXate = \frac{\% \text{ wt } pX \text{ in Xylenes in product} - \text{wt \% } pX \text{ in Xylenes in feed}}{\% \text{ wt } pX \text{ in Xylene at equilibrium} - \text{wt \% } pX \text{ in Xylenes in feed}} \times 100\%$$

TABLE 1

| Catalyst of example | EB conversion | pXate |
|---|---|---|
| 1 (5% ZSM-12) | 4.6 | 74.0 |
| 2 (10% ZSM-12; 25% ZSM-5) | 25.0 | 92.9 |
| 3 (5% ZSM-12; 5% EU-1 (33)) | 35.2 | 95.5 |
| 4 (5% ZSM-12; 5% nano EU-1 (33)) | 35.0 | 96.6 |
| 5 (10% ZSM-12; 5% EU-1 (33)) | 41.5 | 96.0 |
| 6 (5% ZSM-12; 13% EU-1 (33)) | 35.5 | 96.8 |
| 7 (5% ZSM-12; 13% EU-1 (100)) | 23.2 | 95.6 |
| 8 (5% ZSM-12; 13% ZSM-50) | 14.9 | 94.4 |
| 9 (5% ZSM-12; 13% TNU-10) | 19.7 | 88.1 |

That which is claimed is:

1. A catalyst composition which comprises a carrier material component and a metal(s) component that is supported on the carrier material component, wherein the carrier material component comprises (i) a ZSM-12 type zeolite in an amount of from 2 to 20% wt, based on total weight of carrier material, the ZSM-12 type zeolite having a silica to alumina molar ratio in the range of from 60 to 200; (ii) a EU-1 type zeolite in an amount of from 2 to 30% wt, based on total weight of carrier material, the EU-1 type zeolite having a silica to alumina molar ratio in the range of from 20 to 200; and an inorganic binder in an amount in the range of from 55 to 96% wt, based on total weight of carrier material; and wherein the metal(s) component comprises a group VIII metal in an amount of at least 0.01% wt, based on total weight of catalyst.

2. The catalyst according to claim 1, wherein the ZSM-12 type zeolite is present in an amount in the range of from 2 to 15% wt, based on total weight of carrier material.

3. The catalyst according to claim 1, wherein the EU-1 type zeolite is present in an amount in the range of from 2 to 24% wt, based on total weight of carrier material.

4. The catalyst according to claim 1, wherein the inorganic binder is present in an amount in the range of from 70 to 95% wt, based on total weight of carrier material.

5. The catalyst according to claim 1, wherein the inorganic binder consists of alumina.

6. The catalyst according to claim 1, wherein the Group VIII metal is platinum which is present in an amount in the range of from 0.1 to 0.6% wt, based on total weight of catalyst.

7. The catalyst according to claim 1, wherein the ZSM-12 type zeolite has a silica to alumina molar ratio in the range of from 70 to 150.

8. The catalyst according to claim 1, wherein the EU-1 type zeolite has a silica to alumina molar ratio in the range of from 30 to 95.

9. The catalyst according to claim 1, wherein the ZSM-12 type zeolite has an average particle size in the range of from 5 to 50 nm.

10. The catalyst according to claim 1, wherein the EU-1 type zeolite has an average particle size in the range of from 20 to 70 nm.

11. A process for preparing an ethylbenzene conversion catalyst, wherein said process comprises the steps of:
(a) mixing ZSM-12 type zeolite having a silica to alumina molar ratio in the range of from 60 to 200, EU-1 type zeolite having a silica to alumina molar ratio in the range of from 20 to 200, and an inorganic binder to provide a mixture;
(b) shaping said mixture to provide a shaped mixture;
(c) calcining said shaped mixture to provide a calcined carrier;
(d) impregnating said calcined carrier with a Group VIII metal to provide a metal impregnated carrier; and
(e) calcining said metal impregnated carrier;
wherein said ZSM-12 type zeolite is present in said calcined carrier in an amount of from 2 to 20% wt, said EU-1 type zeolite is present in said calcined carrier in an amount of from 2 to 30% wt, said inorganic binder is present in said calcined carrier in an amount of from 55 to 96% wt and said Group VIII metal is present in said ethylbenzene conversion catalyst in an amount of at least 0.01% wt.

12. A process for the isomerisation of alkylaromatics comprising contacting a hydrocarbon feedstock which comprises alkylaromatics with a catalyst as defined in claim 1.

13. The process according to claim 12, wherein the feed comprises ethylbenzene and xylenes.

14. A process as recited in claim 11, wherein said inorganic binder in said mixture provides for an amount of said inorganic binder in the range of from 80 to 91% wt, based on the total weight of said calcined carrier, wherein said ZSM-12 type zeolite in said mixture provides for an amount of said ZSM-12 type zeolite in the range of from 2 to 15% wt, based on the total weight of said calcined carrier, and said EU-1 type zeolite in said mixture provides for an amount of said EU-1 type zeolite in the range of from 2 to 24% wt, based on the total weight of said calcined carrier.

15. A process as recited in claim 14, wherein calcining step (c) is carried out at a calcination temperature in the range of from 450 to 1100° C.

16. A process as recited in claim 15, wherein said Group VIII metal is platinum impregnated into said calcined carrier by impregnating step (d) in an amount of at least 0.01% wt, based on the total weight of said ethylbenzene conversion catalyst.

17. A process as recited in claim 16, wherein said ZSM-12 type zeolite of said calcined carrier has an SAR in the range of from 604e-20070 to 150 and said EU-1 type zeolite of said calcined carrier has an SAR in the range of from 20 to 150.

18. A process as recited in claim 17, wherein said inorganic binder is alumina.

19. A process as recited in claim 18, wherein said ethylbenzene conversion catalyst comprises said calcined carrier having from 4 to 11% wt of said ZSM-12 type zeolite, from 4 to 15% wt of said EU-1 type zeolite, and from 80 to 91% wt of said inorganic binder, with each % wt based on the total weight of said calcined carrier; and said Group VIII metal in an amount in the range of from 0.1 to 0.6% wt, based on the total weight of said ethylbenzene conversion catalyst.

* * * * *